US007157445B2

(12) United States Patent
Sanderink et al.

(10) Patent No.: US 7,157,445 B2
(45) Date of Patent: Jan. 2, 2007

(54) ADMINISTRATION OF ENOXAPARIN SODIUM TO PATIENTS WITH SEVERE RENAL IMPAIRMENT

(75) Inventors: Ger-Jan C. M. Sanderink, Marolles-en-Brie (FR); Santosh Vetticaden, Pleasanton, CA (US); Hans Peter Bacher, Long Grove, IL (US)

(73) Assignees: Aventis Pharma S.A., Cedex (FR); Aventis Pharmaceuticals Inc., Bridgewater, NJ (US)

( * ) Notice: Subject to any disclaimer, the term of this patent is extended or adjusted under 35 U.S.C. 154(b) by 385 days.

(21) Appl. No.: 10/788,041

(22) Filed: Feb. 27, 2004

(65) Prior Publication Data

US 2005/0192252 A1  Sep. 1, 2005

Related U.S. Application Data

(63) Continuation-in-part of application No. 10/786,161, filed on Feb. 26, 2004.

(51) Int. Cl.
*A61K 31/727* (2006.01)
*A61P 7/02* (2006.01)

(52) U.S. Cl. .................................................. 514/56
(58) Field of Classification Search ............. None
See application file for complete search history.

(56) References Cited

OTHER PUBLICATIONS

Drug Facts and Comparisons (56th Ed. 2002), pp. 171-174.*
Aghassarian et al., "A Comparative Pharmacodynamic Study of Anti-Xa Activity to Evaluate the Accumulation Effect of Tinzaparin and Enoxaparin Given at Prophylactic Dose Over 8 Days in Medical Elderly Patients with Impaired Renal Function," *Blood*, vol. 106(11), pt. 2, p. 118b, Abstract 4152 (Nov. 16, 2005).
Leri et al., "Current Enoxaparin Dosing Strategies Yield Supretherapeutic Anti-Xa Activity in Many Elderly Patients," *Journal of the American College of Cardiology*, vol. 43(5), Suppl. A, p. 509A, Abstract 1141-190 (Mar. 3, 2004).
Bacher et al., "Postoperative Monitoring of Low Molecular Weight Heparin Prophylaxis in High-Risk Patients," *Seminars in Thrombosis and Hemostasis*, vol. 19, Supp. 1', pp. 73-78 (1993).
Bazinet et al., "Dosage of Enoxaparin Among Obese and Renal Impairment Patients," *Thrombosis Research*, vol. 116, pp. 41-50 (2005).
Becker et al., "Excess Body Weight Does Not Adversely Influence Either Bioavailability or Anticoagulant Activity of Enoxaparin Administered Subcutaneously in Acute Coronary Syndromes," Suppl. to Circulation, 102, pp. II-427-II-428 (2000).
Lopez-Sanchez et al., "Enoxaparin, Retroperitoneal Haematoma in the Elderly and Imparied Renal Function," *Anaesthesia and Intensive Care*, vol. 33(5), pp. 689-690, (Oct. 2005). pp. 689-690.
Darius et al., "Antithrombotische Therapie mit Niedermolekularen Heparinen bei Niereninsuffizien," *Journal für kerdiologie: Österreichische Zei*, vol. 11(7-8), pp. 313-316 (2004).
Desjardins et al., "Correlation of Plasma Coagulation Parameters With thromboprophylaxis, Patient Characteristics, and Outcome in the MEDENOX Study," *Arch. Pathol. Lab. Med.*, vol. 128, pp. 519-526, (May 2004). p. 519-526.
Farooq et al., "Serious Adverse Incidents With the Usage of Low Molecular Weight Heparins in Patients With Chronic Kidney Disease," *American Journal of Kidney Diseases*, vol. 43(3), pp. 531-537 (Mar. 2004).
Gouin-Thibault et al., "Safety Profile of Different Low-Molecular Weight Heparins Used at Therapeutic Dose," *Drug Safety*, vol. 28(4), pp. 333-349 (2005).
Green et al., "Dosing strategy for enoxaparin in patients with rental impairment presenting with acute coronary syndromes," *British Journal of Clinical Pharmacology*, vol. 59(3), pp. 281-290 (2004).
Horvitz, M.M. et al., "Enoxaparin injection intervention for patients with severe renal impairment," *Pharm.D*, vol. 25(3), p. 481, (Mar. 2005). pp. 481, Abstract 179.
Hulot et al., "Dosing strategy in patients with renal failure receiving enoxaparin for the treatment of non-ST—segment elevation acute coronary syndrome," *Clin. Pharmacol. Ther.*, vol. 77, pp. 542-552 (2005).
Hulot et al., "Effect of Renal Function on the Pharmacokinetics of Enoxaparin and Consequences on Dose Adjustment," *Ther. Drug Monit.*, vol. 26(3), pp. 305-310, (Jun. 2004). pp. 305-310.
Jaffer et al., "Prevention of Venous Thromboembolism in the Geriatric Patient," *Clin. Geriatr. Med.*, vol. 22, pp. 93-111 (2006).
Jones et al., "Pharmacoeconomics of Low-Molecular-Weight Heparins: Limitations of Studies Comparing Them to Unfractionated Heparin", *Expert Opin. Pharmacother.*, vol. 5(9), pp. 1887-1897 (Sep. 2004).

(Continued)

*Primary Examiner*—Johann Richter
*Assistant Examiner*—Frank I Choi
(74) *Attorney, Agent, or Firm*—Finnegan, Henderson, Farabow, Garrett & Dunner, L.L.P.

(57) ABSTRACT

Methods having novel enoxaparin sodium dosing regimens for patients with severe renal impairment are disclosed. The methods may be used for one or more of preventing thrombotic episodes, treating thrombotic episodes, preventing postoperative venous thrombosis, controlling thrombosis and/or decreasing blood hypercoagulation and/or hemorrhaging risks, treating unstable angina, and treating non-Q-wave myocardial infarction in human patients with severe renal impairment. The methods of preventing thrombotic episodes, treating thrombotic episodes, preventing postoperative venous thrombosis, and controling thrombosis and/or decreasing blood hypercoagulation and/or hemorrhaging risks, comprise administering from more than 20 mg to less than 40 mg, from 25 mg to 35 mg, about 30 mg, or 30 mg of enoxaparin sodium to the patient once daily. The methods of treating unstable angina, and non-Q-wave myocardial infarction, comprise administering from more than 0.5 mg/kg body weight to less than 1.5 mg/kg body weight, or about 1 mg/kg body weight of enoxaparin sodium once daily. Articles of manufacture comprising enoxaparin sodium and instructions for the use of the enoxaprin sodium are also disclosed.

36 Claims, 2 Drawing Sheets

OTHER PUBLICATIONS

Kruse et al., "Retrospective evaluation of a pharmacokinetic program for adjusting enoxaparin in renal impairment," *American Heart Journal*, vol. 148(4), pp. 582-589, (Oct. 2004), pp. 582-589.

Nagge and Huh, Letter to the Editor, *Am Heart J*, 149:e21 (2005).

Uthamalingam et al., "Enoxaparin-Associated Spontaneous Retroperitoneal Hematoma in Elderly Patients With Impaired Creatinine Clearance: A Report of Two Cases," *JAGS*, vol. 52(3), pp. 477-479, (Mar. 2004).

Conde-Martel et al., "Spontaneous Retroperitoneal Hematomas in Elderly Patients Treated With Low-Molecular-Weight Heparins," *JAGS*, vol. 53(3), pp. 548-549, (Mar. 2005).

Liboux et al., "Enoxaprin Pharmokinetics and Pharmacodynamics After Intravenous Bolus Administration Alone and at Initiation of a Subcutaneous Dosing Regimen," *Journal of the American College of Cardiology*, Abstract 1106-129, p. 373A, Abstract 1106-129 (2000).

Lojewski et al., "Evaluation of Hemostatic and Fibrinolytic Alterations Associated with Daily Administration of Low-Molecular-Weight Heparin for a 12-Week Period," *Seminars in Thrombosis and Hemostasis*, vol. 21 (2), pp. 228-239 (1995).

Ma et al., "Anti-Xa Monitoring of Enoxaparin for Acute Coronary Syndromes in Patients with Renal Disease," *The Annals of Pharmacotherapy*, vol. 38, pp. 1576-1581, (Oct. 2004). pp. 1576-1581.

Macie et al., "Dosing Practices and Risk Factors for Bleeding in Patients Receiving Enoxaparin for the Treatment of an Acute Coronary Syndrome," *CHEST*, vol. 125 (5), pp. 1616-1621 (2004).

Martin, J. L, "Reliable Anticoagulation with Enoxaparin in Patients Undergoing Percutaneous Coronary Intervention: Final PEPCI Trial Results," *The American Journal of Cardiology*, Abstract TCT-409, pp. 158H-159H (2002).

Martin et al., "Reliable Anticoagulation With Enoxaparin in Patients Undergoing Percutaneous Conorary Intervention: The Pharmacokinetics of Enoxaparin in PCI (PEPCI) Study," *Catheterization and Cardiovascular Interventions*, vol. 61, pp. 163-170 (2004).

Peng et al., "Renal Function, Peak Anti-Xa Levels and Enoxaparin Dosing," *Journal of Pharmacy Practice and Research*, vol. 34(1), pp. 14-17, (2004). pp. 14-17.

Product Monograph, Lovenox, Aventis Pharma Inc., and Notice of Compliance, Feb. 28, 2003.

Reply to the Letter to the Editor, *Am. Heart J.*, 149:e23-e-24, (Mar. 2005).

"Heparin Contraindicated in Severe Renal Impairment," *WHO Drug Information*, vol. 19(1), pp. 24-25, (2005).

Sanderink et al., "Enoxaparin Pharmacokinetics and Pharmacodynamics in Renal Impairment," *Journal of the American College of Cardiology*, 37(2), Abstract 1076-169, p. 229-A (2001).

Siguret et al.,"Low molecular weight heparin treatment in elderly subjects with or without renal insufficiency: new insights between Jun. 2002 and Mar. 2004," *Curr. Opin. Pulm. Med.*, vol. 10, pp. 366-370 (2004).

Thorevska et al., "Anticoagulation in Hospitalized Patients With Renal Insufficiency, A Comparison of Bleeding Rates With Unfractionated Heparin vs Enoxaparin," *CHEST*, vol. 125(3), pp. 856-863, (Mar. 2004).

Abdel-Raheem, Majdi M., et al., "Effect of Low-Molecular -Weight Heparin on Potassium Homeostasis," *Pathophysiology of Haemostasis and Thrombosis*, vol. 32, pp. 107-110 (2002).

Alikhan, Raza, et al., "Prevention of Venous Thromboembolism in Medical Patients with Enoxaparin: A Subgroup Analysis of the MEDENOX Study," *Blood Coagulation & Fibrinolysis*, vol. 14(4), pp. 341-346 (2003).

Antman, M. Elliott, et al., "Assessment of the Treatment Effect of Enoxaparin for Unstable Angina/Non-Q-Wave Myocardial Infarction (TIMI 11B -Essence Meta-Analysis," *Circulation*, vol. 100, pp. 1602-1608 (1999).

Antman, M. Elliott, et al., "Enoxaparin Prevents Death and Cardiac Ischemic Events in Unstable Angina/Non-Q-Wave Myocardial Infarction (Results of the Thrombolysis in Myocardial Infarction (TIMI) 11B Trial," *Circulation*, vol. 100, pp. 1593-1601 (1999).

Bara, L., et al., "Pharmacokinetics of Low Molecular Weight Heparins," *Acta Chir Scand Suppl.*, vol. 543, pp. 65-72 (1998).

Barrett, J.S., et al., "Population Pharmacodynamics in Patients Receiving Tinzaparin for the Prevention and Treatment of Deep Vein Thrombosis," *International Journal of Clinical Pharmacology and Therapeutics*, vol. 39(10), pp. 431-446 (2001).

Bastani, Bahar, et al., "Prolonged Anti-Factor Xa Level in a Patient with Moderate Renal Insufficiency Receiving Enoxaparin," *American Journal of Nephrology*, vol. 22, pp. 403-404 (2002).

Becker, Richard, et al., "Influence of Patient Characteristics and Renal Function on Factor Xa Inhibition Pharmacokinetics and Pharmacodynamics After Enoxaparin Administration in non-ST-segment Elevation Acute Coronary Syndromes," *American Heart Journal*, vol. 143(5), pp. 753-759 (2002).

Berger, Peter B., et al., "Safety and Efficacy of Ticiopidine for Only 2 Weeks After Successful Intracoronary Stent Placement," *Circulation*, pp. 248-253 (1999).

Partial European Search Report for EP 04 29 0530.7, dated Oct. 4, 2004.

PCT International Search Report for PCT/EP2005/002572, dated Feb. 26, 2005.

PCT International Search Report and Written Opinion of the International Searching Authority for PCT/EP2005/002572, dated Jul. 4, 2005.

Boneu, Bernard, et al., "How and When to Monitor a Patient Treated with Low Molecular Weight Heparin," *Seminars in Thrombosis and Hemostasis*, vol. 27(5), Abstracts, pp. 519-522 (2001).

Borawski, Jacek, et al., "Striking Increase in Circulating Hepatocyte Growth Factor During Enoxaparin-Anticoagulated Haemodialysis," *Nephrology Dialysis Transplantation*, vol. 18(8), pp. 1680-1682 (2003).

Brophy, Donald F., et al., "The Pharmacokinetics of Subcutaneous Enoxaparin in End-Stage Renal Disease," *The Journal of Human Pharmacology and Drug Therapy*, vol. 21(2), pp. 169-174 (2001).

Brown, Rex O., et al., "Hyperkalemia Secondary to Concurrent Pharmacotherapy in a Patient Receiving Home Parenteral Nutrition," *Journal of Parenteral and Enteral Nutrition*, vol. 20(6), pp. 429-432 (1996).

Bruno, R., et al., "Population Pharmacokinetics and Pharmacodynamics of Enoxaparin in Unstable Angina and non-ST-segment Elevation Myocardial Infarction," *Br. J. Clin. Pharmacol.*, vol. 56(4)p. 407-414 (2003).

Busby, Leslie T., et al., "Excessive Anticoagulation in Patients with Mild Renal Insufficiency Receiving Long-Term Therapeutic Enoxaparin," *American Journal of Hematology*, vol. 67, pp. 54-56 (2001).

Cadroy, Yves, et al., "Delayed Elimination of Enoxaparine in Patients with Chronic Renal Insufficiency," *Thrombosis Research*, vol. 63, pp. 385-390 (1991).

Casele, Holly L., et al., "Changes in the Pharmacokinetics of the Low-Molecular-Weight Heparin Enoxaparin Sodium During Pregnancy," *American Journal of Obstetrics and Gynecology*, vol. 181(5), pp. 1113-1117 (1999).

Macouilard, Gerard, et al., "Comparative Efficacy of Two Dosages of a Low Molecular Weight Heparin for Prevention of Deep Venous Thrombosis in Spinal Surgery," *Thrombosis and Haemostasis*, vol. 73(6), Abstract 306, p. 979 (1995).

Cavdar, Caner, et al., "Effects of Heparin and Enoxaparin on Lipids and Oxidant System During a Single Haemodialysis Session," *Nephron*, vol. 82, pp. 81-83 (1999).

Cestac, Philippe, et al., "Utilization and Safety of Low Molecular Weight Heparins, "*Drug Safety*, vol. 26(3), pp. 197-207 (2003).

Choussat, Rémi, et al., "A Unique, Low Dose of Intravenous Enoxaparin in Elective Percutaneous Coronary Intervention," *Journal of the American College of Cardiology*, vol. 40(11), pp. 1943-1950 (2002).

Chow, Sheryl L., et al., "Correlation of Antifactor Xa Concentrations with Renal Function in Patients on Enoxaparin," *J. Clin. Pharmacol.*, vol. 43, pp. 586-590 (2003).

Cohen, Marc, et al., "A Comparison of Low-Molecular-Weight Heparin with Unfractioned Heparin for Unstable Coronary Artery Disease," *The New England Journal of Medicine*, vol. 337(7), pp. 447-452 (1997).

Collet, J.Ph., et al., "Enoxaparin in Unstable Angina Patients with Renal Failure," *International Journal of Cardiology*, vol. 80, pp. 81-82 (2001).

Collignon, F., et al., "Comparison of the Pharmacokinetic Profiles of Three Low Molecular Mass Heparins—Dalteparin, Enoxaparin and Nadroparin—Administered Subcutaneously in Healthy Volunteers (Doses for Prevention of Thromboembolism," *Thrombosis and Haemostasis*, pp. 630-640 (1995).

Deitcher, Steven R., "Overview of Enoxaparin in the Treatment of Deep Vein Thrombosis," *The American Journal of Managed Care*, vol. 6(19), pp. S1026-S1033 (2000).

Ellison, J., et al., "Thromboprophylaxis Following Caesarean Section (A Comparison of the Anithrombotic Properties of Three Low Molecular Weight Heparins—Dalteparin, Enoxaparin, and Tinzaparin)," *Thrombosis and Haemostasis*, vol. 86(6), pp. 1374-1378 (2001).

Follea, G., et al., "Pharmacokinetic Studies of Standard Heparin and Low Molecular Weight Heparin in Patients with Chronic Renal Failure," *Haemostasis*, vol. 16, pp. 147-151 (1986).

Frederiksen, S. G., et al., "Enoxaparin Effect Depends on Body-Weight and Current Doses May be Inadequate in Obese Patients," *British Journal of Clinical Pharmacology*, vol. 56(1), pp. 547-548 (2003).

Gerlach, Anthony T., et al., "Enoxaparin and Bleeding Complications: A Review in Patients With and Without Renal Insufficiency," *Pharmacotherapy*, vol. 20(7), pp. 771-775 (2000).

Goudable, C., et al., "Pharmacokinetics of a Low Molecular Weight Heparin (Fraxiparine®) in Various Stages of Chronic Renal Failure," *Nephron*, vol. 59, pp. 543-545 (1991).

Green, Bruce, et al., "Development of a Dosing Strategy for Enoxaparin in Obese Patients," *British Journal of Clinical Pharmacol.* vol. 56, pp. 96-103 (2003).

Henny, Ch. P., et al., "The Effectiveness of a Low Molecular Weight Heparinoid in Chronic Intermittent Haemodialysis," *Thrombosis and Haemostasis*, vol. 54(2), pp. 460-462 (1985).

Holden, D., et al., "Paradoxical Preservation of Renal Function in Patients with Obstructive Uropathy," *The British Journal of Surgery*, vol. 72(5), Abstract 50, p. 408 (1985).

Ip, Beatrice K. H., et al., "A Comparison of the Sensitivity of APTT Reagents to the Effects of Enoxaparin, A Low-Molecular Weight Heparin," *Pathology*, vol. 33, pp. 347-352 (2001).

Ireland, H., et al., "Low Molecular Weight Heparin in Haemodialysis for Chronic Renal Failure: Dose Finding Study of CY222," *Thrombosis and Haemostasis*, vol. 59(2), pp. 240-247 (1998).

Kalus, James S., et al., "Enoxaparin Should Be Used Cautiously in Patients with End-Stage Renal Disease," *Pharmacotherapy*, vol. 21(8), pp. 1015-1016 (2001).

Kaul, Bupesh, et al., "Accidental Spinal Analgesia in the Presence of a Lumboperitoneal Shunt in an Obese Parturient Receiving Enoxaparin Therapy," *Anesthesia & Analgesia*, vol. 95(2), pp. 441-443 (2002).

Khazan, Minou, et al., "Prescribing Patterns and Outcomes of Enoxaparin for Anticoagulation of Atrial Fibrillation," *Pharmacotherapy*, vol. 23(5), pp. 651-658 (2003).

Kim, Karen H., et al., "Enoxaparin-Induced Generalized Exanthem," *Cutis*, vol. 72(1), pp. 57-60 (2003).

Laforest, M.D., et al., "Pharmacokinetics and Biodistribution of Technetium 99m Labeled Standard Heparin and a Low Molecular Weight Heparin (Enoxaparin) After Intravenous Injection in Normal Volunteers," *British Journal of Haematology*, vol. 77, pp. 201-208 (1991).

Lile, James, et al., "Low-Molecular-Weight Heparin Administration in Patients with End-Stage Renal Disease—A Comment," *Pharmacotherapy*, vol. 21(8), pp. 1017-1019 (2001).

Macklon, N.S., et al., "Thrombocytopenia, Antithrombin Deficiency and Extensive Thromboembolism in Pregnancy: Treatment with Low-Molecular-Weight Heparin," *Blood Coagulation and Fibrinolysis*, vol. 6(7), pp. 672-675 (1995).

Macouillard, G., et al., "Prevention of Pulmonary Embolism in Spinal Cord Injured Patients: Comparison of No Fixed-dose Heparin Versus Low Molecular Weight Heparin," *Thrombosis Haemostasis*, vol. 73(6), Abstract 305, p. 978 (1995).

Martindale—The Complete Drug Reference 2003, The Pharmaceutical Press, Enoxaparin Sodium, pp. 885 (XP002299034).

Marzinoto, Velma, et al., "Low Molecular Weight Heparin in Pediatric Patients with Thrombotic Disease," *Presented—International Society Thrombosis and Haemostasis, Jerusalem, Israel* (1995).

Massie, Barry M., "News from the FDA Cardio-renal Advisory Committee Meeting of Jun. 26, 1997," *Circulation*, vol. 96(8) p. 2483 (1997).

Mattiasson, I., et al., "Out-patient Treatment of Acute Deep Vein Thrombosis," *International Angiology*, vol. 17(3), pp. 146-150 (1998).

Melde, Stephen L., "Enoxaparin-Induced Retroperitoneal Hematoma," *The Annals of Pharmacotherapy*, vol. 37(6), pp. 822-824 (2003).

Nurmohamed, M.T., et al., "Comparative Trial of a Low Molecular Weight Heparin (Enoxaparin) for the Prophylaxis of Postoperative Deep Vein Thrombosis in General Surgery," *Thrombosis Haemostasis*, vol. 69(6), Abstract 384, p. 649 (1993).

Naumnik, Beata, et al., "Different Effects of Enoxaparin and Unfractionated Heparin on Extrinsic Blood Coagulation During Haemodialysis: A Prospective Study," *Nephrol Dial Transplant*, vol. 18(7), pp. 1376-1382 (2003).

Noble, Stuart, et al., "Enoxaparin: A Reappraisal of its Pharmacology and Clinical Applications in the Prevention and Treatment of Thromboembolic Disease," *Drugs*, vol. 49(3), pp. 386-410 (1995).

Ozawa, Tsunenori, et al., "Pharmacodynamics and Pharmacokinetics of LMW Heparin in Normal Subjects and Patients with Chronic Renal Insufficiency," *Thrombosis and Haemostasis*, vol. 69(6), Abstract 1149, p. 861 (1993).

Parker, V. et al., "The Effect of Renal Disease on Ardeparin Sodium Pharmacodynamics," *Clinical Pharmacology & Therapeutics*, vol. 53(2), Abstract PII-48, p. 182 (1993).

Press Release, "Aventis Announces Revisions to Lovenox Labeling to Address Obese, Low-Weight and Renally Impaired Patients," Dec. 22, 2003.

Perry D.J., "Treating Venous Thromboembolism: Enoxaparin," *Hospital Medicine*, vol. 62(12), pp. 757-764 (2001).

Piquet, P., et al., "Predictive Enoxaparin (Lovenox) Dosage Regimens in Neonates and Children After Cardiovascular Surgery?," *Thrombosis Haemostasis*, Abstract 281, vol. 73(6). p. 972 (1995).

Polkinghome, Kevan R., et al., "Pharmacokinetic Studies of Dalteparin (Fragmin), Enoxaparin (Clexane), and Danaparoid Sodium (Orgaran) in Stable Chronic Haemodialysis Patients," *American Journal of Kidney Diseases*, vol. 40(5), pp. 990-995 (2002).

Power, G.E., et al., "Retroperitoneal Haematoma Associated with Low Molecular Weight Heparin," *Anaesthesia and Intensive Care*, vol. 30(5), pp. 665-667 (2002).

Priglinger, U., et al., "Prophylactic Anticoagulation with Enoxaparin: Is the Subcutaneous Route Appropriate in the Critically Ill?", *Critical Care Medicine*, vol. 31(5), pp. 1405-1409 (2003).

Rachmani, Rita, et al., "Acute Renal Failure and Paraplegia in a Patient with a Pelvic-Ring Fracture," *Nephrology Dialysis Transplantational*, vol. 15(12), pp. 2050-2052 (2000).

Renaud, H., et al., "Low Molecular Weight Heparin in Haemodialysis and Haemofiltration—Comparison with Unfractionated Heparin," *Proceedings of the European Dialysis and Transplant Association—European Renal Association*, vol. 21, pp. 276-280 (1984).

Rostoker, Guy, et al., "Prevention of Thrombotic Complication of the Nephrotic Syndrome by the Low-Molecular-Weight Heparin Enoxaparin," *Nephron*, vol. 69(20), pp. 20-28 (1995).

Saltissi, David, et al., "Comparison of Low-Molecular-Weight Heparin (Enoxaparin Sodium) and Standard Unfractionated Heparin for Haemodialysis Anticoagulation," *Nephrology Dialysis Transplantation*, vol. 14(11), pp. 2698-2703 (1999).

Samama, M., et al., "Relation Between Weight, Obesity and Frequency of Deep Venous Thrombosis after Enoxaparin in Orthopedic Surgery," *Thrombosis Haemostasis*, vol. 73(6), Abstract 300, p. 977 (1995).

Sanderink, Ger-Jan C.M., et al., "Pharmacokinetics and Pharmacodynamics of the Prophylactic Dose of Enoxaparin Once Daily Over 4 Days in Patients with Renal Impairment," *Thrombosis Research*, vol. 105, pp. 225-231 (2002).

Sanderink, Ger-Jan C.M., et al., "The Pharmacokinetics and Pharmacodynamics of Enoxaparin in Obese Volunteers," *Clinical Pharmacology & Therapeutics*, vol. 72(3), pp. 308-318 (2002).

Scholten, Donald J., et al, "A Comparison of Two Different Prophylactic Dose Regimens of Low Molecular Weight Heparin in Bariatric Surgery," *Obesity Surgery*, vol. 12, pp. 19-24 (2002).

Spinier, Sarah, et al., "Safety and Efficacy of Unfractionated Heparin Versus Enoxaparin in Patients Who are Obese and Patients with Severe Renal Impairment: Analysis from the Essence and TIMI 11B Studies," *American Heart Journal*, vol. 146(1), pp. 33-41 (2003).

Streif, W., et al., "Use of Low Molecular Mass Heparin (Enoxaparin) in Newborn Infants: A Prospective Cohort Study of 62 Patients," *Arch. Dis. Child Fetal Neonatal. Ed.*, vol. 88, pp. F365-F370 (2003).

Tryba, M., et al., "Central Neuraxial Block and Low Molecular Weight Heparin (Enoxaparine): Lessons Learned from Different Dosage Regimes in Two Continents," *Acta Anaesthesiologica Scandina Vica*, vol. 41, M37, pp. 100-104 (1997).

U.S. Department of Health and Human Services Food and Drug Administration, "Guidance of Industry—Pharmacokinetics in Patients with Impaired Renal Function—Study Design, Data Analysis, and Impact on Dosing and Labeling" (1998).

Vaccaro, Sharon, et al., "Single-Dose Pharmacodynamic Comparison of a Subcutaneous 40 MG Dose of Enoxaparin in Healthy and Renally Impaired Subjects," *Pharmacotherapy, Boston, US*, vol. 21, No. 2, XP008035680 (2002).

Van Biljoh, I., et al., "Low Molecular Weight Heparin for Anticoagulation During Haemodialysis in Children—A Preliminary Study," *European Journal of Pediatrics*, vol. 155(1) p. 70 (1996).

Wallentin, L., et al., "Efficacy and Safety of Tenecteplase in Combination with the Low-Molecular-Weight Heparin Enoxaparin or Unfractionaed Heparin in the Prehospital Setting," *Circulation*, vol. 108(2), pp. 135-142 (2003).

http://www.medscape.com/viewarticle/436030.

http://www.nzhpa.org.nz/qum.htm.

\* cited by examiner

FIG. 1

OBSERVED AND SIMULATED PHARMACOKINETIC PROFILES IN SEVERE RENALLY IMPAIRED PATIENTS AND NORMAL VOLUNTEERS (30 mg q12h).

FIG. 2

ADMINISTRATION OF ENOXAPARIN SODIUM TO PATIENTS WITH SEVERE RENAL IMPAIRMENT

This application is a continuation-in-part of application Ser. No. 10/786,161, filed Feb. 26, 2004 now abandoned.

Broadly, this invention is directed to novel dosing regimens for administering enoxaparin sodium (sometimes referred to hereinafter as "enoxaparin") to patients with severe renal impairment. The invention also relates to methods of using such dosing regimens of enoxaparin for one or more of preventing thrombotic episodes, treating thrombotic episodes, preventing postoperative venous thrombosis, controlling thrombosis and/or decreasing blood hypercoagulation and/or hemorrhaging risks, treating unstable angina, and treating non-Q-wave myocardial infarction, in human patients with severe renal impairment (creatinine clearance <30 mL/min), defined herein. This invention also provides articles of manufacture for use in connection with a patient with severe renal impairment, comprising enoxaparin and instructions designed to achieve administration of the enoxaparin.

Enoxaparin sodium is available from Aventis under the trademark Lovenox® (Clexane® in some other countries). Enoxaparin sodium exhibits renal clearance. Study data have demonstrated a significant impact of renal function on enoxaparin pharmacokinetics as measured by plasma anti-Xa activity. The main effect of renal impairment is a reduced clearance, which results in a significantly longer elimination half-life. This in turn results in higher pre-dose levels after repeated administration and then an increase in Amax (maximum observed activity) after repeated dosing.

Elevated levels of enoxaparin sodium in patients with severe renal impairment may cause undesirable effects, such as bleeding resulting from excessive anticoagulation. The possibility of a dose adjustment in patients with severe renal impairment has been suggested. A difficulty, however, in determining the appropriate amount of any adjustment in patients with severe renal impairment results from the need to balance the desired antithrombotic activity of enoxaparin sodium against the possibility of excessive bleeding or other undesired results of enoxaparin sodium accumulation.

As used herein, "severe renal impairment" means an impairment of renal function in a patient characterized by a creatinine clearance rate of <30 mL/min. Patients with severe renal impairment may be referred to herein as having severe renal insufficiency or as severely (or severe) renally impaired patients.

The term "prevent," "preventing" and "prevention" refers to the administration of therapy on a prophylactic or preventative basis to an individual who may ultimately manifest at least one symptom of a disease or condition (e.g., thrombosis) but who has not yet done so. Such individuals may be identified on the basis of risk factors that are known to correlate with the subsequent occurrence of the disease. Alternatively, prevention therapy may be administered without prior identification of a risk factor, as a prophylactic measure. Delaying the onset of the at least one symptom may also be considered prevention or prophylaxis.

As used herein the term "treat," "treating" or "treatment" refers to the administration of therapy to an individual who already manifests at least one symptom of a disease or condition (e.g., thrombosis), or who has previously manifested at least one symptom of a disease or condition.

As used herein, "acute illness" refers to any condition, illness, or disease that does or may cause severely restricted mobility, which is or may be characterized by a greater risk for thromboembolic complications than is present in the population generally. Nonlimiting examples include patients with cardiac insufficiency, respiratory failure, severe infections, and rheumatic diseases.

As used herein "enoxaparin sodium" refers to the low molecular weight heparin (LMWH) approved by the U.S. Food and Drug Administration (FDA) as Lovenox® (enoxaparin sodium injection) and any LMWH approved by the FDA pursuant to an application citing Lovenox® (enoxaparin sodium injection) as the listed drug. Enoxaparin sodium is available from Aventis and sold in the United States in the form of enoxaparin sodium injection, under the trademark Lovenox® (Clexane® in some other countries). In general, enoxaparin sodium is obtained by alkaline degradation of heparin benzyl ester derived from porcine intestinal mucosa. Its structure is characterized, for example, by a 2-0-sulfo-4-enepyranosuronic acid group at the non-reducing end and a 2-N,6-0-disulfo-D-glucosamine at the reducing end of the chain. The average molecular weight is about 4500 daltons. The molecular weight distribution is:

| | |
|---|---|
| <2000 daltons | ≦20% |
| 2000 to 8000 daltons | ≧68% |
| >8000 daltons | ≦18% |

Enoxaparin sodium injection is a sterile aqueous solution containing enoxaparin sodium. Enoxaparin sodium injection is available from Aventis at 100 mg/ml in prefilled syringes (30 mg/0.3 mL pre-filled syringes, 40 mg/0.4 mL pre-filled syringes, 60 mg/0.6 mL pre-filled syringes, 80 mg/0.8 mL pre-filled syringes, and 100 mg/1.0 mL pre-filled syringes), graduated prefilled syringes, multiple-dose vials (300 mg/3.0 mL multi-dose vials), and ampoules (30 mg/0.3 mL). Enoxaparin sodium injection 100 mg/mL concentration contains 10 mg enoxaparin sodium (approximate anti-Factor Xa activity of 1000 IU [with reference to the W.H.O. First International Low Molecular Weight Heparin Reference Standard]) per 0.1 mL water for injection. Enoxaparin sodium injection is also available from Aventis at 150 mg/ml in graduated prefilled syringes (90 mg/0.6 mL pre-filled syringes, 120 mg/0.8 mL pre-filled syringes, and 150 mg/1.0 mL pre-filled syringes). Enoxaparin sodium injection 150 mg/mL concentration contains 15 mg enoxaparin sodium (approximate anti-Factor Xa activity of 1500 IU [with reference to the W.H.O. First International Low Molecular Weight Heparin Reference Standard]) per 0.1 mL water for injection.

The enoxaparin sodium injection prefilled syringes and graduated prefilled syringes are preservative-free and intended for use only as a single-dose injection. The multiple-dose vial contains 15 mg/1.0 mL benzyl alcohol as a preservative. The pH of the injection is 5.5 to 7.5. Enoxaparin sodium injection may also be administered in an arterial line for a hemodialysis indication.

Because creatinine is found in stable plasma concentrations, is freely filtered and not reabsorbed, and is minimally secreted by the kidneys, creatinine clearance is used to estimate the glomerular filtration rate (GFR). The GFR in turn is the standard by which kidney function is assessed. The creatinine clearance test compares the level of creatinine in urine with the creatinine level in the blood. Clearance is often measured as milliliters/minute (mL/min). Creatinine clearance values may be calculated by the Cockroft-Gault formula. (Cockcroft and Gault, Nephron, Vol. 16, pp. 31–41 (1976)). In a normal human subject, creatinine clearance is >80 mL/min. Renal impairment is a condition characterized by a creatinine clearance rate of ≦80 mL/min. Severe renal impairment is characterized by a creatinine clearance rate of <30 mL/min.

Known enoxaparin sodium dosage regimens include 30 mg of enoxaparin sodium twice a day (approximately every 12 hours) for patients undergoing hip or knee replacement surgery, and 40 mg of enoxaparin sodium once a day (approximately every 24 hours) for patients undergoing abdominal surgery or medical patients during acute illness.

It has been found that in subjects with severe renal impairment the mean decrease in apparent plasma clearance of enoxaparin-derived anti-Xa activity was 39% and 50% in two studies. This was found to result in a 65% to 95% increase in AUC (area under the plasma activity-time curve to infinity) over one dosing interval at steady state. (After the first dose in one study the increase in AUC(0–24) was only 34%.) Given the observed prolongation of the elimination half-life in severe renal impairment (t1/2λz 15.9 h (severe renal impairment) versus 6.9 h (normal subjects)), a reduction may be provided by a reduction in the dose size or by a longer dosing interval.

Data obtained from both normal volunteers and patients with severe renal impairment were modeled according to a two compartment open pharmacokinetic model with first order absorption and elimination. The following pharmacokinetic parameters were used for simulation: volume of distribution (VD/F)=4,000 mL; K01 (absorption constant) for normal volunteers=0.32 h$^{-1}$; K01 (absorption constant) for patients with severe renal impairment=0.34 h$^{-1}$; K10 (elimination rate constant) for normal volunteers=0.24 h$^{-1}$; K10 (elimination rate constant) for patients with severe renal impairment=0.12 h$^{-1}$; K12 (transfer rate from first compartment to second compartment) for normal volunteers=0.10 h$^{-1}$; K12 (transfer rate from first compartment to second compartment) for patients with severe renal impairment=0.10 h$^{-1}$; K21 (transfer rate from second compartment to central compartment) for normal volunteers=0.18 h$^{-1}$; and K21 (transfer rate from second compartment to central compartment) for patients with severe renal impairment=0.04 h$^{-1}$. Using simulation curves (FIG. 1 (Observed and simulated pharmacokinetic profiles in severe renally impaired patients and normal volunteers (30 mg q12 h)).) and deduced pharmacokinetic parameters (Table 1) for dosages of 30 mg/12 h (30 milligrams/12 hours) in normal patients, and dosages of 15 mg/12 h, 20 mg/12 h, and 30 mg/24 h in patients with severe renal insufficiency, it has been found that adjustment of the 30 mg enoxaparin sodium twice daily dosage to 30 mg enoxaparin sodium once daily combines the advantages of adequate exposure and little accumulation. Using the simulation curves and pharmacokinetic parameters, 20 mg/12 h mimics the profile in normal subjects quite well, but because of the low dosing interval/half-life ratio, achievement of steady-state is expected to be longer and, especially for 15 mg/12 h, exposure at treatment initiation is expected to be low compared to the reference treatment. This may be explained by the relatively lower impact of severe renal impairment on exposure on day 1.

TABLE 1

Figure 1:
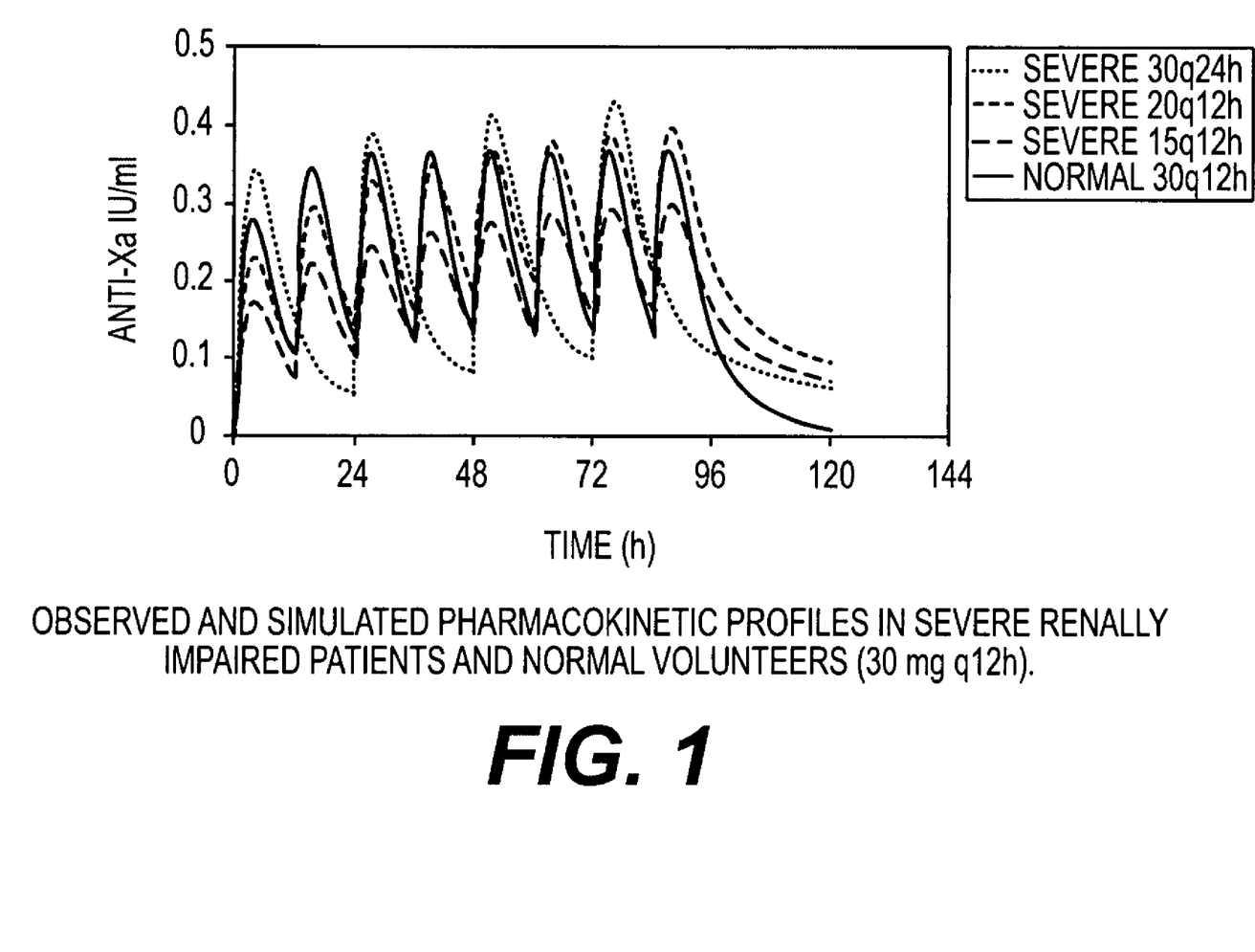
FIG. 1 is a graph comparing the anti-Xa activity over time of enoxaparin sodium administered in normal volunteers at a dose of 30 mg every 12 hours and in severe renally impaired patients in alternative dosage regimens.

Predicted pharmacokinetic parameters in severely renally impaired patients for alternative regimens to 30 mg q 12 h.

|  | Normal 30 q 12 h | Severe 15 q 12 h | Severe 20 q 12 h | Severe 30 q 24 h | |
|---|---|---|---|---|---|
| AUCτ1* | 2.30 | 1.50 | 2.00 | 4.04 | 2.02*** |
| AUC τ8** | 3.12 | 2.89 | 3.86 | 5.91 | 2.95*** |
| Amax τ1 | 0.344 | 0.221 | 0.295 | 0.342 | |
| Amax τ8 | 0.367 | 0.298 | 0.398 | 0.429 | |
| Amin τ1 | 0.123 | 0.103 | 0.138 | 0.053 | |
| Amin τ8 | 0.140 | 0.172 | 0.229 | 0.110 | |
| Rac AUC τ8/τ1 | 1.35 | 1.93 | | 1.46 | |
| Rac Amax | 1.07 | 1.35 | | 1.26 | |

Rac: accumulation ratio.
*τ1: first dosing interval (0–12 h, except severe 30 q 24 h: 0–24 h).
**τ8: 8th dosing interval (84–96 h, except severe 30 q 24 h: 4th interval 72–96 h).
***Average AUC per 12 h on day 1 and day 4, respectively.

Figure 2:
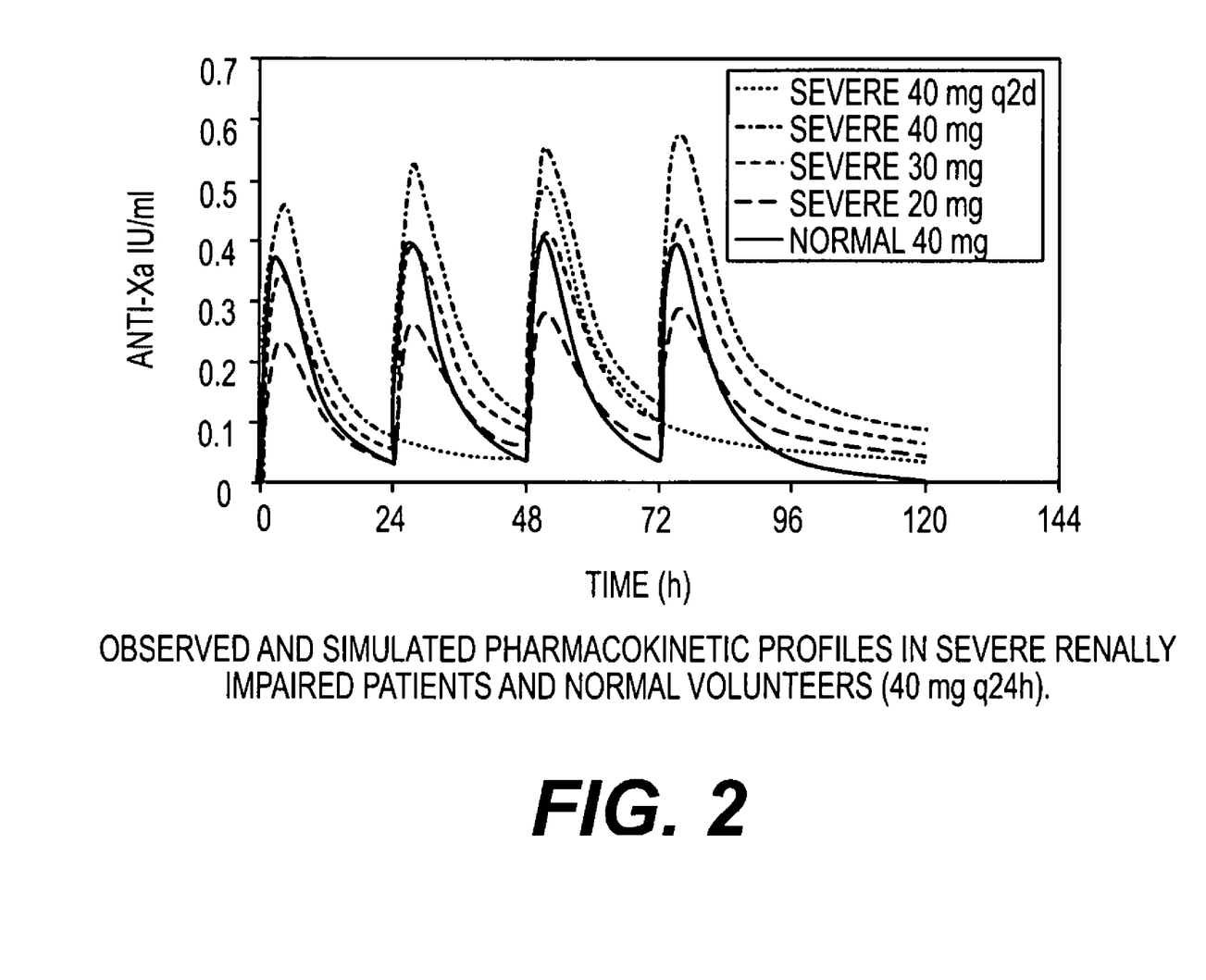
FIG. 2 is a graph comparing the anti-Xa activity over time of enoxaparin sodium administered in normal volunteers at a dose of 40 mg every 24 hours and in severe renally impaired patients in alternative dosage regimens.

For the once-daily regimen of 40 mg, from simulation curves (FIG. 2 (Observed and simulated pharmacokinetic profiles in severe renally impaired patients and normal volunteers (40 mg q24 h)).) and deduced pharmacokinetic parameters (Table 2) for dosages of 40 mg/24 h in normal patients and, and dosages of 20 mg/24 h, 30 mg/24 h, and 40 mg/24 h in patients with sever renal insufficiency, it has been found that 30 mg enoxaparin sodium once daily is desirable considering the whole treatment period; somewhat higher levels than in normal subjects would occur only in the elimination phase, but more adequate exposure than with a 20 mg dose is predicted to be obtained before reaching steady-state. This may be explained by the smaller difference in anti-Xa levels on day 1 (+34% in AUC) than at steady-state (+65%) between severe renally impaired patients and normal subjects observed in one study.

TABLE 2

Predicted pharmacokinetic parameters in severely renally impaired patients for alternative regimens to 40 mg q 24 h.

|  | Normal 40 mg qd | Severe 20 mg qd | Severe 30 mg qd | Severe 40 mg qd | Severe 40 mg q 2 d | |
|---|---|---|---|---|---|---|
| AUCτ1* | 3.87 | 2.70 | 4.06 | 5.41 | 6.62 | 3.31*** |
| AUC τ4** | 4.15 | 3.87 | 5.81 | 7.74 | 7.76 | 3.88*** |
| Amax τ1 | 0.371 | 0.228 | 0.342 | 0.457 | 0.457 | |
| Amax τ4 | 0.394 | 0.287 | 0.430 | 0.574 | 0.491 | |
| Amin τ1 | 0.030 | 0.036 | 0.054 | 0.072 | 0.038 | |
| Amin τ4 | 0.033 | 0.073 | 0.109 | 0.146 | 0.051 | |

TABLE 2-continued

Predicted pharmacokinetic parameters in severely renally impaired patients for alternative regimens to 40 mg q 24 h.

|  | Normal 40 mg qd | Severe 20 mg qd | Severe 30 mg qd | Severe 40 mg qd | Severe 40 mg q 2 d |
|---|---|---|---|---|---|
| Rac AUC | 1.07 |  | 1.43 |  | 1.17 |
| Rac Amax | 1.06 |  | 1.26 |  | 1.08 |

Rac: accumulation ratio.
*τ1: first dosing interval (0–24 h, except severe 40 q 2 d: 0–48 h).
**τ4: 4th dosing interval (72–96 h, except severe 40 q 2 d: 2nd interval 48–96 h).
***Average AUC per day on days 1–2 and days 3–4, respectively.

Given dose-linear exposure of enoxaparin anti-Xa activity, the same rule can apply to treatment doses, i.e., 1 mg/kg once daily as a substitute for both 1 mg/kg twice daily and 1.5 mg/kg once daily.

In an embodiment, the invention provides a method for the prevention of thrombotic episodes in a human patient with severe renal impairment comprising administering to said patient from more than 20 mg to less than 40 mg of enoxaparin sodium once daily. In another embodiment of the method, from 25 mg to 35 mg of enoxaparin sodium is administered once daily. In another embodiment of the method, about 30 mg of enoxaparin sodium is administered once daily. In another embodiment of the method, 30 mg of enoxaparin sodium is administered once daily. In a further embodiment, administration of the enoxaparin sodium begins prior to abdominal surgery, after hip or knee replacement surgery, or before hip replacement surgery. In another embodiment, the patient is a medical patient at risk for thromboembolic complications due to severely restricted mobility during acute illness. Administration of enoxaparin sodium is, for example, by injection, and further for example, by subcutaneous injection.

In another embodiment, the invention provides a method for the treatment of thrombotic episodes in a human with severe renal impairment comprising administering to said patient from more than 20 mg to less than 40 mg of a enoxaparin sodium once daily. In another embodiment of the method, from 25 mg to 35 mg of enoxaparin sodium is administered once daily. In yet another embodiment of the method, about 30 mg of enoxaparin sodium is administered once daily. In another embodiment of the method, 30 mg of enoxaparin sodium is administered once daily. In a further embodiment, administration of enoxaparin sodium begins prior to abdominal surgery, after hip or knee replacement surgery, or before hip replacement surgery. In another embodiment, the patient is a medical patient at risk for thromboembolic complications due to severely restricted mobility during acute illness. Administration of enoxaparin sodium is, for example, by injection and further for example by subcutaneous injection.

In another embodiment, the invention provides a method for the prevention of venous thrombosis in a postoperative human patient with severe renal impairment comprising administering to said patient from more than 20 mg to less than 40 mg of enoxaparin sodium once daily. In another embodiment of the method, from 25 mg to 35 mg of enoxaparin sodium is administered once daily. In another embodiment of the method, about 30 mg of enoxaparin sodium is administered once daily. In yet another embodiment of the method, 30 mg of enoxaparin sodium is administered once daily. In a further embodiment, administration of enoxaparin sodium begins prior to abdominal surgery, after hip or knee replacement surgery, or before hip replacement surgery. In another embodiment, the patient is a medical patient at risk for thromboembolic complications due to severely restricted mobility during acute illness. Administration of enoxaparin sodium is, for example, by injection and further for example by subcutaneous injection.

In another embodiment, the invention provides a therapeutic method for controlling thrombosis and/or decreasing blood hypercoagulation and/or hemorrhaging risks in a patient with severe renal impairment comprising administering to said patient from more than 20 mg to less than 40 mg of enoxaparin sodium once daily. In another embodiment of the method, from 25 mg to 35 mg of enoxaparin sodium is administered once daily. In another embodiment of the method, about 30 mg of enoxaparin sodium is administered once daily. In yet another embodiment of the method, 30 mg of enoxaparin sodium is administered once daily. In a further embodiment, administration of enoxaparin sodium begins prior to abdominal surgery, after hip or knee replacement surgery, or before hip replacement surgery. In another embodiment, the patient is a medical patient at risk for thromboembolic complications due to severely restricted mobility during acute illness. Administration of enoxaparin sodium is, for example, by injection and further for example by subcutaneous injection.

In providing enoxaparin sodium dosage regimens for patients with severe renal impairment, the dosage regimen for administration of enoxaparin sodium is based on the particular indication. For each indication, methods are provided herein that include methods for preventing and/or treating thrombotic episodes in a human patient, methods for preventing venous thrombosis in a postoperative human patient, and methods for controlling thrombosis and/or decreasing blood hypercoagulation and/or hemorrhaging risks in a patient.

In patients undergoing abdominal surgery who are at risk for thromboembolic complications, the initial dose of enoxaparin sodium is administered before abdominal surgery. Enoxaparin sodium is, for example, administered beginning approximately 2 hours prior to surgery. After the initial dose, the dosage can be administered once daily (approximately every 24 hours). Administration can be continued, for example, for approximately 7 to 10 days, and further for example, up to approximately 12 days. The dosage of enoxaparin sodium is, for example, from more than 20 mg to less than 40 mg, from 21 mg to 39 mg, from 22 mg to 38 mg, from 23 mg to 37 mg, from 24 mg to 36 mg, from 25 mg to 35 mg, from 26 mg to 34 mg, from 27 mg to 33 mg, from 28 mg to 32 mg, from 29 mg to 31 mg, about 30 mg, or 30 mg. Administration of enoxaparin sodium is, for example, by injection, and further for example, by subcutaneous injection.

An embodiment of the invention thus provides a method for the prevention of thrombotic episodes in a human patient with severe renal impairment comprising administering to said patient from more than 20 mg to less than 40 mg of enoxaparin sodium once daily beginning prior to abdominal surgery. In another embodiment, the method comprises administering to said patient from 25 mg to 35 mg of enoxaparin sodium once daily beginning prior to abdominal surgery. In another embodiment, the method comprises administering about 30 mg of enoxaparin sodium once daily beginning prior to abdominal surgery. In a further embodiment, the method comprises administering to said patient 30 mg of enoxaparin sodium by subcutaneous injection once daily beginning prior to abdominal surgery.

An embodiment of the invention also provides a method for treatment of thrombotic episodes in a human patient with severe renal impairment comprising administering to said patient from more than 20 mg to less than 40 mg of enoxaparin sodium once daily beginning prior to abdominal surgery. In another embodiment, the method comprises administering to said patient from 25 mg to 35 mg of enoxaparin sodium once daily beginning prior to abdominal surgery. In yet another embodiment, the method comprises administering about 30 mg of enoxaparin sodium once daily beginning prior to abdominal surgery. In a further embodiment, the method comprises administering to said patient 30 mg of enoxaparin sodium by subcutaneous injection once daily beginning prior to abdominal surgery.

An embodiment of the invention also provides a method for the prevention of venous thrombosis in a postoperative human patient with severe renal impairment comprising administering to said patient from more than 20 mg to less than 40 mg of enoxaparin sodium once daily beginning prior to abdominal surgery. In another embodiment, the method comprises administering to said patient from 25 mg to 35 mg of enoxaparin sodium once daily beginning prior to abdominal surgery. In yet another embodiment, the method comprises administering about 30 mg of enoxaparin sodium once daily beginning prior to abdominal surgery. In a further embodiment, the method comprises administering to said patient 30 mg of enoxaparin sodium by subcutaneous injection once daily beginning prior to abdominal surgery.

An embodiment of the invention also provides a therapeutic method for controlling thrombosis and/or decreasing blood hypercoagulation and/or hemorrhaging risks in a human patient with severe renal impairment comprising administering to said patient from more than 20 mg to less than 40 mg of enoxaparin sodium once daily beginning prior to abdominal surgery. In another embodiment, the method comprises administering to said patient from 25 mg to 35 mg of enoxaparin sodium once daily beginning prior to abdominal surgery. In yet another embodiment, the method comprises administering about 30 mg of enoxaparin sodium once daily beginning prior to abdominal surgery. In a further embodiment, the method comprises administering to said patient 30 mg of enoxaparin sodium by subcutaneous injection once daily.

In patients undergoing hip or knee replacement surgery, the initial dose of enoxaparin sodium can be administered approximately 12 to 24 hours after surgery, provided that hemostasis has been established. The dosage can be administered once daily (approximately every 24 hours), for example, for approximately 7 to 10 days, and further for example, for up to approximately 14 days. The dosage of enoxaparin sodium is, for example, from more than 20 mg to less than 40 mg, from 21 mg to 39 mg, from 22 mg to 38 mg, from 23 mg to 37 mg, from 24 mg to 36 mg, from 25 mg to 35 mg, from 26 mg to 34 mg, from 27 mg to 33 mg, from 28 mg to 32 mg, from 29 mg to 31 mg, about 30 mg, or 30 mg. Administration of enoxaparin sodium can be, for example, by injection, and further for example, by subcutaneous injection.

An embodiment of the invention provides a method for the prevention of thrombotic episodes in a human patient with severe renal impairment comprising administering to said patient from more than 20 mg to less than 40 mg of enoxaparin sodium once daily beginning after hip of knee replacement surgery. In another embodiment, the method comprises administering to said patient from 25 mg to 35 mg of enoxaparin sodium once daily beginning after hip of knee replacement surgery. In yet another embodiment, the method comprises administering about 30 mg of enoxaparin sodium once daily beginning after hip of knee replacement surgery. In a further embodiment, the method comprises administering to said patient 30 mg of enoxaparin sodium by subcutaneous injection once daily beginning after hip of knee replacement surgery.

An embodiment of the invention also provides a method for treatment of thrombotic episodes in a human patient with severe renal impairment comprising administering to said patient from more than 20 mg to less than 40 mg of enoxaparin sodium once daily beginning after hip of knee replacement surgery. In another embodiment, the method comprises administering to said patient from 25 mg to 35 mg of enoxaparin sodium once daily beginning after hip of knee replacement surgery. In another embodiment, the method comprises administering about 30 mg of enoxaparin sodium once daily beginning after hip of knee replacement surgery. In a further embodiment, the method comprises administering to said patient 30 mg of enoxaparin sodium by subcutaneous injection once daily beginning after hip of knee replacement surgery.

An embodiment of the invention also provides a method for the prevention of venous thrombosis in a postoperative human patient with severe renal impairment comprising administering to said patient from more than 20 mg to less than 40 mg of enoxaparin sodium once daily beginning after hip of knee replacement surgery. In another embodiment, the method comprises administering to said patient from 25 mg to 35 mg of enoxaparin sodium once daily beginning after hip of knee replacement surgery. In yet another embodiment, the method comprises administering about 30 mg of enoxaparin sodium once daily beginning after hip of knee replacement surgery. In a further embodiment, the method comprises administering to said patient 30 mg of enoxaparin sodium by subcutaneous injection once daily beginning after hip of knee replacement surgery.

An embodiment of the invention also provides a therapeutic method for controlling thrombosis and/or decreasing blood hypercoagulation and/or hemorrhaging risks in a human patient with severe renal impairment comprising administering to said patient from more than 20 mg to less than 40 mg of enoxaparin sodium once daily beginning after hip of knee replacement surgery. In another embodiment, the method comprises administering to said patient from 25 mg to 35 mg of enoxaparin sodium once daily beginning after hip of knee replacement surgery. In another embodiment, the method comprises administering about 30 mg of enoxaparin sodium once daily beginning after hip of knee replacement surgery. In a further embodiment, the method comprises administering to said patient 30 mg of enoxaparin sodium by subcutaneous injection once daily beginning after hip of knee replacement surgery.

For hip replacement surgery patients, a dose of enoxaparin sodium may be administered approximately 12 (±3) hours prior to surgery. Following this initial phase of thromboprophylaxis, the dosage can be, for example, administered once daily (approximately every 24 hours) for approximately 3 weeks (approximately 21 days). The dosage of enoxaparin sodium is, for example, from more than 20 mg to less than 40 mg, from 21 mg to 39 mg, from 22 mg to 38 mg, from 23 mg to 37 mg, from 24 mg to 36 mg, from 25 mg to 35 mg, from 26 mg to 34 mg, from 27 mg to 33 mg, from 28 mg to 32 mg, from 29 mg to 31 mg, about 30 mg, or 30 mg. Administration of enoxaparin sodium can be, for example, by injection, and further for example, by subcutaneous injection.

An embodiment of the invention provides a method for the prevention of thrombotic episodes in a human patient with severe renal impairment comprising administering to said patient from more than 20 mg to less than 40 mg of enoxaparin sodium once daily beginning approximately 12 hours before hip replacement surgery. In another embodiment, the method comprises administering to said patient from 25 mg to 35 mg of enoxaparin sodium once daily beginning approximately 12 hours before hip replacement surgery. In another embodiment, the method comprises administering about 30 mg of enoxaparin sodium once daily beginning approximately 12 hours before hip replacement surgery. In a further embodiment, the method comprises administering to said patient 30 mg of enoxaparin sodium by subcutaneous injection once daily beginning approximately 12 hours before hip replacement surgery.

An embodiment of the invention also provides a method for the prevention of thrombotic episodes in a human patient with severe renal impairment comprising administering to said patient from more than 20 mg to less than 40 mg of enoxaparin sodium once daily beginning approximately 12 hours before hip replacement surgery. In another embodiment, the method comprises administering to said patient from 25 mg to 35 mg of enoxaparin sodium once daily beginning approximately 12 hours before hip replacement surgery. In yet another embodiment, the method of the invention comprises administering about 30 mg of enoxaparin sodium once daily beginning approximately 12 hours before hip replacement surgery. In a further embodiment, the method comprises administering to said patient 30 mg of enoxaparin sodium by subcutaneous injection once daily beginning approximately 12 hours before hip replacement surgery.

An embodiment of the invention also provides a method for the prevention of venous thrombosis in a postoperative human patient with severe renal impairment comprising administering to said patient from more than 20 mg to less than 40 mg of enoxaparin sodium once daily beginning approximately 12 hours before hip replacement surgery. In another embodiment, the method comprises administering to said patient from 25 mg to 35 mg of enoxaparin sodium once daily beginning approximately 12 hours before hip replacement surgery. In yet another embodiment, the method comprises administering about 30 mg of enoxaparin sodium once daily beginning approximately 12 hours before hip replacement surgery. In a further embodiment, the method comprises administering to said patient 30 mg of enoxaparin sodium by subcutaneous injection once daily beginning approximately 12 hours before hip replacement surgery.

An embodiment of the invention also provides a therapeutic method for controlling thrombosis and/or decreasing blood hypercoagulation and/or hemorrhaging risks in a human patient with severe renal impairment comprising administering to said patient from more than 20 mg to less than 40 mg of enoxaparin sodium once daily beginning approximately 12 hours before hip replacement surgery. In another embodiment, the method comprises administering to said patient from 25 mg to 35 mg of enoxaparin sodium once daily beginning approximately 12 hours before hip replacement surgery. In yet another embodiment, the method comprises administering about 30 mg of enoxaparin sodium once daily beginning approximately 12 hours before hip replacement surgery. In a further embodiment, the method comprises administering to said patient 30 mg of enoxaparin sodium by subcutaneous injection once daily beginning approximately 12 hours before hip replacement surgery.

For medical patients with severe renal impairment at risk for thromboembolic complications due to severely restricted mobility during acute illness, such as patients with cardiac insufficiency, respiratory failure, severe infections, and rheumatic diseases, enoxaparin sodium may be administered once daily. The dosage is, for example, administered once daily (approximately every 24 hours), such as, for approximately 6 to 11 days, and further for example, up to approximately 14 days. The dosage of enoxaparin sodium is, for example, from more than 20 mg to less than 40 mg, from 21 mg to 39 mg, from 22 mg to 38 mg, from 23 mg to 37 mg, from 24 mg to 36 mg, from 25 mg to 35 mg, from 26 mg to 34 mg, from 27 mg to 33 mg, from 28 mg to 32 mg, from 29 mg to 31 mg, about 30 mg, or 30 mg. Administration of enoxaparin sodium can be, for example, by injection, and further for example, by subcutaneous injection.

An embodiment of the invention provides a method for the prevention of thrombotic episodes in a human patient with severe renal impairment during acute illness comprising administering to said patient from more than 20 mg to less than 40 mg of enoxaparin sodium once daily. In another embodiment, the method comprises administering to said patient from 25 mg to 35 mg of enoxaparin sodium once daily. In yet another embodiment, the method comprises administering about 30 mg of enoxaparin sodium once daily. In a further embodiment, the method comprises administering to said patient 30 mg of enoxaparin sodium by subcutaneous injection once daily.

Another embodiment of the invention also provides a method for the treatment of thrombotic episodes in a human patient with severe renal impairment during acute illness comprising administering to said patient from more than 20 mg to less than 40 mg of enoxaparin sodium once daily. In another embodiment, the method comprises administering to said patient from 25 mg to 35 mg of enoxaparin sodium once daily. In yet another embodiment, the method comprises administering about 30 mg of enoxaparin sodium once daily. In a further embodiment, the method comprises administering to said patient 30 mg of enoxaparin sodium by subcutaneous injection once daily.

An embodiment of the invention also provides a method for the prevention of venous thrombosis in a human patient with severe renal impairment during acute illness comprising administering to said patient from more than 20 mg to less than 40 mg of enoxaparin sodium once daily. In another embodiment, the method comprises administering to said patient from 25 mg to 35 mg of enoxaparin sodium once daily. In yet another embodiment, the method comprises administering about 30 mg of enoxaparin sodium once daily. In a further embodiment, the method comprises administering to said patient 30 mg of enoxaparin sodium by subcutaneous injection once daily.

An embodiment of the invention also provides a method for controlling thrombosis and/or decreasing blood hypercoagulation and/or hemorrhaging risks in a human patient with severe renal impairment during acute illness comprising administering to said patient from more than 20 mg to less than 40 mg of enoxaparin sodium once daily. In another embodiment, the method comprises administering to said patient from 25 mg to 35 mg of enoxaparin sodium once daily. In yet another embodiment, the method comprises administering about 30 mg of enoxaparin sodium once daily. In a further embodiment, the method comprises administering to said patient 30 mg of enoxaparin sodium by subcutaneous injection once daily.

In patients suffering from unstable angina or non-Q-wave myocardial infarction a dose of enoxaparin sodium can be administered once daily. The dosage can be administered for a minimum of 2 days and continued until clinical stabilization. The dosage can be, for example, administered for 2 to 8 days, and further for example up to about 12.5 days. The dosage can be, for example, from more than 0.5 mg/kg to less than 1.5 mg/kg, from 0.6 mg/kg to 1.4 mg/kg, from 0.7 mg/kg to 1.3 mg/kg, from 0.8 mg/kg to 1.2 mg/kg, from 0.9 mg/kg to 1.1 mg/kg about 1 mg/kg, or 1 mg/kg. Kg refers to body weight of the patient in kilograms. Administration can, for example, be by injection, and further for example by subcutaneous injection. Administration of the enoxaparin sodium may be accompanied, for example, by concurrent once daily administration of approximately 100 to 325 mg of aspirin.

An embodiment of the invention provides a method for treatment of unstable Angina and non-Q-wave myocardial infarction in a patient with severe renal impairment comprising administering to said patient from more than 0.5 mg/kg body weight to less than 1.5 mg/kg body weight of enoxaparin sodium once daily. In an embodiment of the method, about 1 mg/kg body weight of enoxaparin sodium can be administered once daily. In a further embodiment of the method, 1 mg/kg body weight of enoxaparin sodium can be administered by subcutaneous injection once daily. In another embodiment of the method, approximately 100 to 325 mg of aspirin can also be administered concurrently once daily.

In outpatient treatment of patients with acute deep vein thrombosis without pulmonary embolism who can be treated at home, inpatient (hospital) treatment of patients with acute deep vein thrombosis with pulmonary embolism, or inpatient (hospital) treatment of patients with acute deep vein thrombosis without pulmonary embolism who are not candidates for outpatient treatment, a dose of enoxaparin sodium can be administered once daily. The dosage can be administered for a minimum of 5 days and until a therapeutic oral anticoagulant effect has been achieved (International Normalization Ratio 2.0 to 3.0). The dosage can be, for example, administered for about 7 days and may be administered up to about 17 days. The dosage can be, for example, from more than 0.5 mg/kg to less than 1.5 mg/kg, from 0.6 mg/kg to 1.4 mg/kg, from 0.7 mg/kg to 1.3 mg/kg, from 0.8 mg/kg to 1.2 mg/kg, from 0.9 mg/kg to 1.1 mg/kg about 1 mg/kg, or 1 mg/kg. Kg refers to the body weight of the patient in kilograms. Administration can be, for example, by injection, and further for example, by subcutaneous injection. Administration of the enoxaparin sodium can be done in conjunction with daily administration of warfarin sodium therapy initiated within about 72 hours of the initiation of enoxaparin sodium administration.

An embodiment of the invention provides a method for outpatient treatment of patients with severe renal impairment with acute deep vein thrombosis without pulmonary embolism who can be treated at home, inpatient (hospital) treatment of patients with severe renal impairment and with acute deep vein thrombosis with pulmonary embolism, or inpatient (hospital) treatment of patients with severe renal impairment and with acute deep vein thrombosis without pulmonary embolism who are not candidates for outpatient treatment, comprising administering to said patient from more than 0.5 mg/kg body weight to less than 1.5 mg/kg body weight of enoxaparin sodium once daily. In an embodiment of the method, about 1 mg/kg body weight of enoxaparin sodium is administered once daily. In a further embodiment of the method, 1 mg/kg body weight of enoxaparin sodium is administered by subcutaneous injection once daily. In another embodiment of the method, warfarin sodium therapy is initiated within about 72 hours of the initiation of enoxaparin sodium administration and provided in conjunction therewith.

Articles of manufacture for use in administering a dosage regimen of enoxaparin sodium to a patient with severe renal impairment are also provided. The article of manufacture comprises enoxaparin sodium and instructions for administering the enoxaparin sodium to the patient. The instructions are designed to achieve administration of a dosage regimen of enoxaparin sodium to the patient. The actual dosage regimen for administration is based on the particular indication.

Articles of manufacture for use in connection with the prevention or treatment of thrombotic episodes in a human patient with severe renal impairment by the methods of the invention comprise enoxaparin sodium and instructions (e.g., label, labeling, or package insert) for administering the enoxaparin sodium to the patient, said instructions being designed to achieve administration to said patient of a dosage of enoxaparin sodium once daily. The dosage of enoxaparin sodium is, for example, from more than 20 mg to less than 40 mg, from 21 mg to 39 mg, from 22 mg to 38 mg, from 23 mg to 37 mg, from 24 mg to 36 mg, from 25 mg to 35 mg, from 26 mg to 34 mg, from 27 mg to 33 mg, from 28 mg to 32 mg, or from 29 mg to 31 mg, about 30 mg, or 30 mg. The enoxaparin sodium is, for example, contained within a vial, and further for example, contained within a prefilled syringe. The prefilled syringe and instructions are, for example, contained within a suitable package. The enoxaparin sodium can be, for example, administered by injection, and further for example, administered by subcutaneous injection.

An embodiment of the invention provides an article of manufacture for use in connection with the prevention of thrombotic episodes in a human patient with severe renal impairment comprising enoxaparin sodium and instructions designed to achieve administration to said patient of from more than 20 mg to less than 40 mg of the enoxaparin sodium once daily. In another embodiment, the article of manufacture comprises enoxaparin sodium and instructions designed to achieve administration to said patient of 25 mg to 35 mg of enoxaparin sodium once daily. In yet another embodiment the article of manufacture comprises enoxaparin sodium and instructions designed to achieve administration to said patient of about 30 mg of enoxaparin sodium once daily. In a further embodiment of the article of manufacture, the enoxaparin sodium is contained within a syringe and the instructions are designed to achieve administration to said patient of 30 mg of the enoxaparin sodium by subcutaneous injection once daily.

An embodiment of the invention provides an article of manufacture for use in connection with the treatment of thrombotic episodes in a human patient with severe renal impairment comprising enoxaparin sodium and instructions designed to achieve administration to said patient of from more than 20 mg to less than 40 mg of the enoxaparin sodium once daily. In another embodiment, the article of manufacture comprises enoxaparin sodium and instructions designed to achieve administration to said patient of 25 mg to 35 mg of enoxaparin sodium once daily. In yet another embodiment, the article of manufacture comprises enoxaparin sodium and instructions designed to achieve administration to said patient of about 30 mg of enoxaparin sodium once daily. In a further embodiment of the article of manufacture, the enoxaparin sodium is contained within a syringe and the instructions are designed to achieve administration to said patient of 30 mg of the enoxaparin sodium by subcutaneous injection once daily.

Articles of manufacture for use in connection with the treatment of unstable angina or non-Q-wave myocardial infarction in a human patient with severe renal impairment by the methods of the invention comprise enoxaparin sodium and instructions (e.g., label, labeling, or package insert) for the use thereof, said instructions being designed to achieve administration to said patient of a dosage of enoxaparin sodium once daily. The dosage is, for example, from more than 0.5 mg/kg to less than 1.5 mg/kg, from 0.6 mg/kg to 1.4 mg/kg, from 0.7 mg/kg to 1.3 mg/kg, from 0.8 mg/kg to 1.2 mg/kg, from 0.9 mg/kg to 1.1 mg/kg about 1 mg/kg, or 1 mg/kg. Kg refers to the body weight of the patient in kilograms. The enoxaparin sodium is, for example, contained within a vial, and further for example, contained within a prefilled syringe. The syringe and instructions for using the syringe, which delivers the desired dosage, are, for example, contained within a suitable package. The enoxaparin sodium is, for example, administered by injection, and further for example, administered by subcutaneous injection. Administration of the enoxaparin sodium may, for example, be accompanied by daily concurrent administration of approximately 100 to 325 mg of aspirin.

An embodiment of the invention provides an article of manufacture for use in connection with the treatment of unstable angina or non-Q-wave myocardial infarction in a human patient with severe renal impairment comprising enoxaparin sodium and instructions designed to achieve administration of from more than 0.5 mg/kg body weight to less than 1.5 mg/kg body weight of the enoxaparin sodium once daily. In another embodiment, the article of manufacture of the invention comprises enoxaparin sodium and instructions designed to achieve administration of about 1 mg/kg body weight of the enoxaparin sodium once daily. In a further embodiment of the article of manufacture, the enoxaparin sodium is contained within a prefilled syringe and the instructions direct the use of the syringe to achieve administration of 1 mg/kg body weight of the enoxaparin sodium to the patient by subcutaneous injection once daily. Administration of the enoxaparin sodium may, for example, be accompanied by daily concurrent administration of approximately 100 to 325 mg of aspirin.

Articles of manufacture for use in connection with the treatment of a patient with acute deep vein thrombosis without pulmonary embolism who can be treated at home, inpatient (hospital) treatment of patients with acute deep vein thrombosis with pulmonary embolism, or inpatient (hospital) treatment of patients with acute deep vein thrombosis without pulmonary embolism who are not candidates for outpatient treatment, comprise enoxaparin sodium and instructions (e.g., label, labeling, or package insert) for achieving administration of a dosage of enoxaparin sodium once daily. The dosage is, for example, from more than 0.5 mg/kg to less than 1.5 mg/kg, from 0.6 mg/kg to 1.4 mg/kg, from 0.7 mg/kg to 1.3 mg/kg, from 0.8 mg/kg to 1.2 mg/kg, from 0.9 mg/kg to 1.1 mg/kg about 1 mg/kg, or 1 mg/kg. Kg refers to the body weight of the patient in kilograms. The enoxaparin sodium is, for example, contained within a vial, and further for example, contained within a prefilled syringe. The prefilled syringe and instructions to achieve the desired administration, are, for example, contained within a suitable package. The enoxaparin sodium can be, for example, administered by injection, and further for example, administered by subcutaneous injection. Administration of the enoxaparin sodium may, for example, be accompanied by daily concurrent administration of warfarin sodium therapy initiated within about 72 hours of the initiation of enoxaparin sodium administration.

An embodiment of the invention provides an article of manufacture for use in connection with the treatment of patients with acute deep vein thrombosis without pulmonary embolism who can be treated at home, inpatient (hospital) treatment of patients with acute deep vein thrombosis with pulmonary embolism, or inpatient (hospital) treatment of patients with acute deep vein thrombosis without pulmonary embolism who are not candidates for outpatient treatment, in a human patient with severe renal impairment, comprising enoxaparin sodium and instructions for achieving administration of from more than 0.5 mg/kg body weight to less than 1.5 mg/kg body weight of the enoxaparin sodium once daily. In another embodiment, the article manufacture comprises enoxaparin sodium and instructions for achieving administration of about 1 mg/kg body weight of the enoxaparin sodium once daily. In a further embodiment of the article of manufacture, the enoxaparin sodium is contained within a prefilled syringe and instructions for use of the prefilled syringe, designed to achieve administration of 1 mg/kg body weight of the enoxaparin sodium to the patient by subcutaneous injection once daily. In another embodiment of the article of manufacture, administration of the enoxaparin sodium is, for example, accompanied by daily concurrent administration of warfarin sodium therapy initiated within about 72 hours of the initiation administration of the heterogenous admixture of sulfated heparinic polysaccharides.

It will be readily apparent to one of ordinary skill in the relevant arts that other suitable modifications and adaptations to the methods and applications described herein are suitable and may be made without departing from the scope of the invention or any embodiment thereof. Having now described the present invention in detail, the same will be more clearly understood by reference to the following examples of the invention, which are based on pharmacokinetic modeling and are included herewith for purposes of illustration only and are not intended to be limiting of the invention.

EXAMPLES

Example 1

Administration of Enoxaparin Sodium to Prevent or Treat Thrombotic Episodes in a Human Patient with Severe Renal Impairement A patient having severe renal impairment can be identified by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 30 mg of enoxaparin sodium is subcutaneously injected into the patient once daily.

Example 2

Administration of Enoxaparin Sodium to Prevent or Treat Thrombotic Episodes in a Human Patient with Severe Renal Impairement Who is Undergoing Abdominal Surgery A patient who is undergoing abdominal surgery can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 30 mg of enoxaparin sodium is subcutaneously injected into the patient once daily, beginning approximately 2 hours prior to abdominal surgery. After the initial dose, the dosage is administered once daily (approximately every 24 hours) for approximately 7 to 10 days.

Example 3

Administration of Enoxaparin Sodium to Prevent or Treat Thrombotic Episodes in a Human Patient with Severe Renal Impairement Who is Undergoing Hip or Knee Replacement Surgery A patient who is undergoing hip or knee replacement surgery can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 30 mg of enoxaparin sodium is subcutaneously injected into the patient once daily, beginning approximately 12 to 24 hours after surgery, provided that hemostasis has been established. The dosage is thereafter administered once daily (approximately every 24 hours) for approximately 7 to 10 days.

Example 4

Administration of Enoxaparin Sodium to Prevent or Treat Thrombotic Episodes in a Human Patient with Severe Renal Impairement Who is Undergoing Hip Replacement Surgery A patient who is undergoing hip replacement surgery can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 30 mg of enoxaparin sodium is subcutaneously injected into the patient once daily, beginning approximately 12 (±3) hours prior to surgery. Following this initial phase of thromboprophylaxis, the dosage is administered once daily (approximately every 24 hours) for approximately 3 weeks (approximately 21 days).

Example 5

Administration of Enoxaparin Sodium to Prevent or Treat Thrombotic Episodes in a Human Patient with Severe Renal Impairement During Acute Illness A patient with acute illness can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 30 mg of enoxaparin sodium is subcutaneously injected into the patient once daily (approximately every 24 hours) for approximately 6 to 11 days.

Example 6

Administration of Enoxaparin Sodium to Treat Unstable Angina or Non-Q-Wave Myocardial Infarction in a Human Patient with Severe Renal Impairment A patient with unstable angina or non-Q-wave myocardial infarction can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 1 mg/kg (of the patient's body weight) of enoxaparin sodium is subcutaneously injected once daily for a minimum of 2 days and continued until clinical stabilization (approximately 2 to 8 days).

Example 7

Administration of Enoxaparin Sodium to Treat Acute Deep Vein Thrombosis With or Without Pulmonary Embolism in a Human Patient with Severe Renal Impairment A patient with acute deep vein thrombosis without pulmonary embolism who can be treated at home, a patient with acute deep vein thrombosis with pulmonary embolism who can be treated on an inpatient (hospital) basis, or a patient with acute deep vein thrombosis without pulmonary embolism who is not a candidate for outpatient treatment and is treated on an inpatient (hospital) basis, can be identified as having severe renal impairment by the creatinine clearance test, by comparing the level of creatinine in the patient's urine with the creatinine level in the patient's blood. Clearance is measured in mL/min, and creatinine clearance values calculated by the Cockroft-Gault formula. (Cockcroft and Gault, Nephron, Vol. 16, pp. 31–41 (1976)). Based on the results of the creatinine clearance test, patients with a creatinine clearance value <30 mL/min are identified as having severe renal failure.

A sterile aqueous solution containing 1 mg/kg (of the patient's body weight) of enoxaparin sodium is subcutaneously injected into the patient once daily for 5 to about 7 days, until a therapeutic oral anticoagulant effect has been achieved (International Normalization Ratio 2.0 to 3.0).

While the administration of enoxaparin sodium to patients with severe renal failure has been described in connection with certain embodiments, it is not intended to limit the invention to the particular forms set forth, but on the contrary, it is intended to cover such alternatives, modifications and equivalents as may be included within the spirit and scope of the invention as defined by the following claims.

What is claimed is:

1. A method for the prevention of thrombotic episodes in a postoperative human patient with severe renal impairment, comprising administering to said patient 30 mg of enoxaparin sodium by subcutaneous injection once daily, beginning approximately two hours prior to abdominal surgery.

2. A method as recited in claim 1, wherein said administration is continued for approximately 7–10 days.

3. A method for the treatment of thrombotic episodes in a postoperative human patient with severe renal impairment, comprising administering to said patient 30 mg of enoxaparin sodium by subcutaneous injection once daily, beginning approximately two hours prior to abdominal surgery.

4. A method as recited in claim 3, wherein said administration is continued for approximately 7–10 days.

5. A method for the prevention of venous thrombosis in a postoperative human patient with severe renal impairment, comprising administering to said patient 30 mg of enoxaparin sodium by subcutaneous injection once daily, beginning approximately two hours prior to abdominal surgery.

6. A method as recited in claim 5, wherein said administration is continued for approximately 7–10 days.

7. A therapeutic method for controlling thrombosis and/or decreasing blood hypercoagulation and/or hemorrhaging risks in a postoperative human patient with severe renal impairment, comprising administering to said patient 30 mg of enoxaparin sodium by subcutaneous injection once daily, beginning approximately two hours prior to abdominal surgery.

8. A method as recited in claim 7, wherein said administration is continued for approximately 7–10 days.

9. A method for the prevention of thrombotic episodes in a human patient with severe renal impairment, comprising administering to said patient 30 mg enoxaparin sodium by subcutaneous injection once daily, beginning approximately 12 to 24 hours after hip or knee replacement surgery.

10. A method as recited in claim 9, wherein said administration is continued for approximately 7–10 days.

11. A method for the treatment of thrombotic episodes in a human patient with severe renal impairment, comprising administering to said patient 30 mg of enoxaparin sodium by subcutaneous injection once daily, beginning approximately 12 to 24 hours after hip or knee replacement surgery.

12. A method as recited in claim 11, wherein said administration is continued for approximately 7–10 days.

13. A method for the prevention of venous thrombosis in a human patient with severe renal impairment, comprising administering to said patient 30 mg of enoxaparin sodium by subcutaneous injection once daily, beginning approximately 12 to 24 hours after hip or knee replacement surgery.

14. A method as recited in claim 13, wherein said administration is continued for approximately 7–10 days.

15. A therapeutic method for controlling thrombosis and/or decreasing blood hypercoagulation and/or hemorrhaging risks in a postoperative human patient with severe renal impairment, comprising administering to said patient 30 mg of enoxaparin sodium by subcutaneous injection once daily, beginning approximately 12 to 24 hours after hip or knee replacement surgery.

16. A method as recited in claim 15, wherein said administration is continued for approximately 7–10 days.

17. A method for the prevention of thrombotic episodes in a human patient with severe renal impairment, comprising administering to said patient 30 mg of enoxaparin sodium by subcutaneous injection once daily, beginning 12 hours before hip replacement surgery.

18. A method as recited in claim 17, wherein said administration is continued for approximately three weeks.

19. A method for the treatment of thrombotic episodes in a human patient with severe renal impairment, comprising administering to said patient 30 mg of enoxaparin sodium by subcutaneous injection once daily, beginning 12 hours before hip replacement surgery.

20. A method as recited in claim 19, wherein said administration is continued for approximately three weeks.

21. A method for the prevention of venous thrombosis in a postoperative human patient with severe renal impairment, comprising administering to said patient 30 mg of enoxaparin sodium by subcutaneous injection once daily, beginning 12 hours before hip replacement surgery.

22. A method as recited in claim 21, wherein said administration is continued for approximately three weeks.

23. A therapeutic method for controlling thrombosis and/or decreasing blood hypercoagulation and/or hemorrhaging risks in a human patient with severe renal impairment, comprising administering to said patient 30 mg of enoxaparin sodium by subcutaneous injection once daily, beginning 12 hours before hip replacement surgery.

24. A method as recited in claim 23, wherein said administration is continued for approximately three weeks.

25. A method for the prevention of thrombotic episodes in a human patient with severe renal impairment during acute illness, comprising administering to said patient 30 mg of enoxaparin sodium by subcutaneous injection once daily.

26. A method as recited in claim 25, wherein said administration is continued for approximately 6 to 11 days.

27. A method for the treatment of thrombotic episodes in a human patient with severe renal impairment during acute illness, comprising administering to said patient 30 mg of enoxaparin sodium by subcutaneous injection once daily.

28. A method as recited in claim 27, wherein said administration is continued for approximately 6 to 11 days.

29. A method for the prevention of venous thrombosis in a postoperative human patient with severe renal impairment during acute illness, comprising administering to said patient 30 mg of enoxaparin sodium by subcutaneous injection once daily.

30. A method as recited in claim 29, wherein said administration is continued for approximately 6 to 11 days.

31. A therapeutic method for controlling thrombosis and/or decreasing blood hypercoagulation and/or hemorrhaging risks in a human patient with severe renal impairment during acute illness, comprising administering to said patient 30 mg of enoxaparin sodium by subcutaneous injection once daily.

32. A method as recited in claim 31, wherein said administration is continued for approximately 6 to 11 days.

33. A method for the prevention of thrombotic episodes in a human patient with severe renal impairment, comprising administering to said patient 30 mg of enoxaparin sodium by subcutaneous injection once daily.

34. A method for the treatment of thrombotic episodes in a human patient with severe renal impairment, comprising administering to said patient 30 mg of enoxaparin sodium by subcutaneous injection once daily.

35. A method for the prevention of venous thrombosis in a postoperative human patient with severe renal impairment, comprising administering to said patient 30 mg of enoxaparin sodium by subcutaneous injection once daily.

36. A therapeutic method for controlling thrombosis and/or decreasing blood hypercoagulation and/or hemorrhaging risks in a patient with severe renal impairment, comprising administering to said patient 30 mg of enoxaparin sodium by subcutaneous injection once daily.

* * * * *